United States Patent [19]
Poku et al.

[11] Patent Number: 5,827,970
[45] Date of Patent: Oct. 27, 1998

[54] NON-DESTRUCTIVE METHOD OF DETERMINING SUBSTRATE TILT WITHIN A PACKAGED SEMICONDUCTOR COMPONENT

[75] Inventors: Isaac T. Poku, Austin; Rama P. Cherkur, Cedar Park, both of Tex.; Yushi Matsuda, Sendai, Japan

[73] Assignee: Motorola Inc., Schaumburg, Ill.

[21] Appl. No.: 724,285

[22] Filed: Sep. 16, 1996

[51] Int. Cl.⁶ .................................................. G01N 29/10
[52] U.S. Cl. ............................... 73/620; 73/629; 438/14; 438/15
[58] Field of Search .................... 257/666, 676, 257/678, 701, 787; 437/180, 209, 217, 220; 364/507, 490, 508; 73/597, 598, 599, 600, 602, 606, 609, 610, 614, 618, 620, 629; 438/14–15

[56] References Cited

U.S. PATENT DOCUMENTS

| | | | |
|---|---|---|---|
| 4,518,992 | 5/1985 | Kessler et al. | 358/112 |
| 4,618,934 | 10/1986 | Nagase | 364/507 |
| 4,741,212 | 5/1988 | Rehwald | 73/600 |
| 4,866,986 | 9/1989 | Cichanski | 73/600 |
| 5,406,849 | 4/1995 | Drescher-Krasicka et al. | 73/588 |
| 5,600,068 | 2/1997 | Kessler et al. | 73/620 |

OTHER PUBLICATIONS

Sonix, Inc., Sonix IC Inspection System, "HS1000 HiS-PEED ™ Scanning Acoustic Microscope".

Moore, Thomas A., "SAM provides critical IC inspection," Reprinted from the Oct. 1990 issue of *Advanced Materials & Processes*.

Sonix, Inc., Micro–Scann IC Inspection System, Scanning Acoustic Microscope for the Inspection of Integrated Circuits.

"Plastic Integrated Circuit Package for the C–SAM," presentation by Cavalry Technology to Motorola, Inc.; May 27, 1992, pp. 1–8.

Sonix, Inc., "Scanning Acoustic Microscope Fundametals," pp. 1–15; 1–8.

Sonix, Inc., "IC3.1 Acoustic Microscope Software Users Guide and Information Manual," Version 3.10h, Oct. 1994, pp. 1–1 through 9–7.

*Primary Examiner*—Hezron Williams
*Assistant Examiner*—Rose M. Miller
*Attorney, Agent, or Firm*—Jeffrey S. Abel

[57] ABSTRACT

A non-destructive method of determining substrate tilt within a packaged component includes providing the packaged component (10) with a component surface (32), providing a substrate (22) in the packaged component (10) wherein the substrate (22) has a substrate surface (33), using an acoustic wave (50) to measure a distance (34) between the component surface (32) and a region on the substrate surface (33), using another acoustic wave (53) to measure another distance (35) between the component surface (32) and a different region on the substrate surface (33), and comparing the distances (34, 35) to a threshold value.

20 Claims, 4 Drawing Sheets

NON-DESTRUCTIVE METHOD OF DETERMINING SUBSTRATE TILT WITHIN A PACKAGED SEMICONDUCTOR COMPONENT

BACKGROUND OF THE INVENTION

This invention relates, in general, to substrate tilt, and more particularly, to non-destructive methods of determining substrate tilt within a packaged component.

A semiconductor die is typically mounted on a die pad portion of a leadframe, wire bonded to leads of the leadframe, and then packaged using a high pressure transfer molding technique. However, the high pressure transfer molding technique often tilts the semiconductor die and the die pad. Consequently, the die tilt often stretches and breaks the wire bonds, exposes the wire bonds outside of the semiconductor package, or causes various other problems.

The die tilt is typically measured by physically cutting open the semiconductor package to reveal a cross-section of the component. Then, the degree of die tilt is optically measured from the cross-section. However, this conventional measuring technique is labor intensive because several hours are typically required to complete the cutting and measuring operations. Furthermore, this conventional measuring technique is destructive because physically cutting open the semiconductor package destroys the component. Therefore, this die tilt measurement method is not compatible with a manufacturing process because the measurement technique is too time consuming and because the semiconductor component must be discarded after measuring the degree of die tilt.

Accordingly, a need exists for a method of determining substrate tilt within a packaged component wherein the method is non-destructive and can be integrated into a manufacturing process. The method should also be fast so that the cycle time for fabricating a semiconductor component is not significantly increased.

DETAILED DESCRIPTION OF THE DRAWINGS

Figure 1:
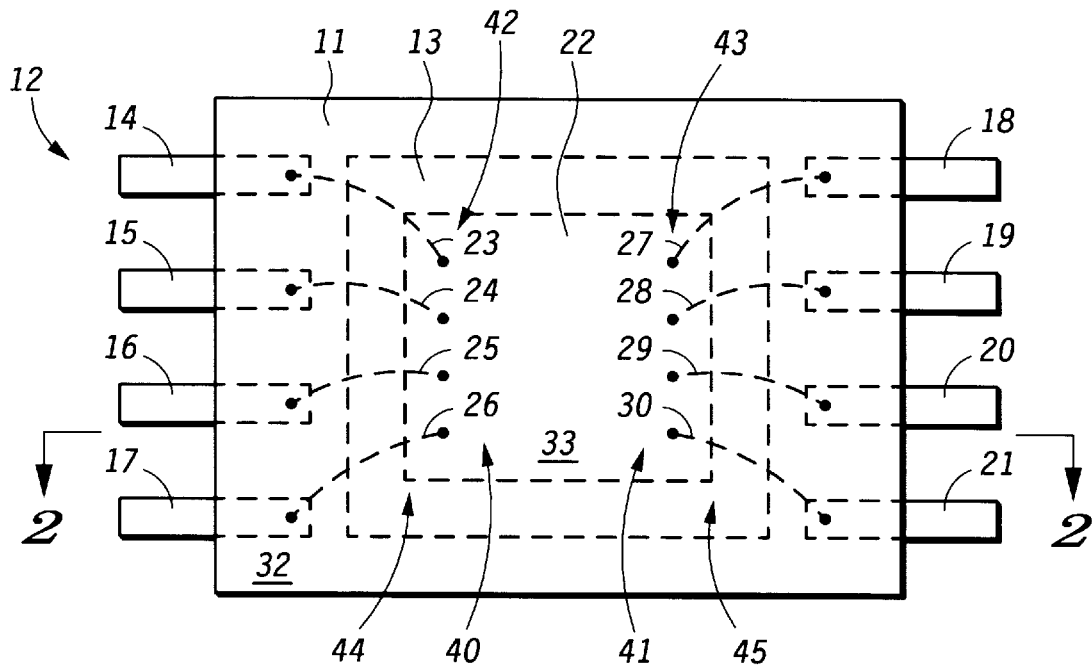
FIG. 1 illustrates a top view of a packaged semiconductor component in accordance with the present invention.
Figure 2:
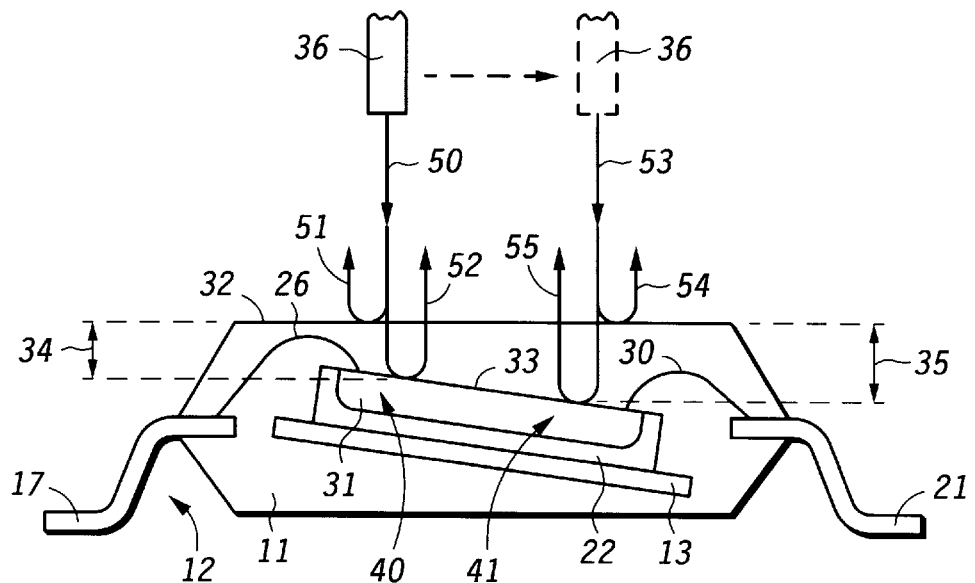
FIG. 2 portrays a cross-sectional view of the packaged semiconductor component taken along a section line 2—2 of FIG. 1 in accordance with the present invention.

FIG. 1 illustrates a top view of a packaged semiconductor component 10, and FIG. 2 portrays a cross-sectional view of component 10 taken along a section line 2—2 of FIG. 1. Elements of FIG. 2 that have the same reference numerals as FIG. 1 are the same as the corresponding FIG. 1 elements. As explained in more detail hereinafter, a transducer 36 in FIG. 2 is not shown in FIG. 1 to facilitate the explanation of component 10.

Component 10 includes a device substrate 22 that is mounted on a support substrate 13. Substrate 22 can be comprised of a semiconductor material including, but not limited to, silicon or gallium arsenide. Substrate 22 has a surface 33 that faces away from substrate 13, and substrate 22 also has a plurality of ends 44 and 45, which are at opposite sides of substrate 22. End 44 has a plurality of opposite corners 40 and 42, and end 45 has a plurality of opposite corners 41 and 43 wherein surface 33 couples together ends 44 and 45 and corners 40, 41, 42, and 43. A semiconductor device or integrated circuit 31 (FIG. 2) is manufactured or fabricated in substrate 22 using semiconductor processing techniques known to those skilled in the art. Because circuit 31 can have many different structures, the depicted structure is only for the purpose of illustrating circuit 31.

Substrate 13 is a portion of a leadframe 12, which also includes a plurality of leads 14, 15, 16, 17, 18, 19, 20, and 21. Substrate 13 is also known in the art as a flag or a pad, which can have a plurality of ends and corners underlying the ends and corners described earlier for substrate 22. It is understood that leadframe 12 is not restricted to the embodiment depicted in FIGS. 1 and 2. Instead, leadframe 12 can be any available leadframe used in the art. Accordingly, leadframe 12 is comprised of conventional leadframe materials. Substrate 22 is coupled, attached, or adhered to substrate 13 using processes known in the art, and substrate 22 is conventionally wire-bonded to the leads of leadframe 12. More specifically, circuit 31 is electrically coupled to leads 14, 15, 16, 17, 18, 19, 20, and 21 via wire bonds 23, 24, 25, 26, 27, 28, 29, and 30, respectively.

Substrate 22, substrate 13, and interior portions of the leads of leadframe 12 are encapsulated or packaged in a conventional plastic package 11. Package 11 can be formed around substrates 13 and 22 by using a high pressure transfer molding technique known in the art. Package 11 has an exterior, outer, or top surface 32 (FIG. 2) and can have ends and corners overlying the ends and corners described earlier for substrate 22. An interface exists between surface 33 of substrate 22 and the mold compound used to form package 11.

Next, a non-destructive method of evaluating, detecting, or determining substrate tilt within package 11 or component 10 is performed. The non-destructive method uses acoustic or sound waves to detect a tilt or slope in substrates 13 or 22. Therefore, component 10 is still electrically functional after the tilt measurement. The use of acoustic waves to characterize an internal component is known in the art as sonography. Specific types of sonographic techniques suitable for semiconductor applications include scanning acoustic tomography (SAT) techniques and scanning acoustic microscopy (SAM) techniques. Commercially available sonographic tools include a Sonix HS1000 HiSpeed™ Acoustic Scanning Microscope and a Plastic Integrated Circuit Package (PIC-Pac) SAM, which are sold by Sonix Incorporated of Springfield, Va. and Sonoscan of Bensenville, Ill., respectively.

In order to determine substrate tilt, at least two distances 34 and 35 (FIG. 2) are acoustically measured between surface 32 and the interface between surface 33 and package 11 wherein distances 34 and 35 are measured near different ones of the corners of substrate 22. If the substrate tilt is to be determined in two dimensions, then only two distances are preferably measured to reduce the cycle time required for this analytical technique. However, if the substrate tilt is to be determined in three dimensions, then only three distances are preferably measured for similar reasons. Additional distances can be measured to improve the accuracy of the two or three dimensional tilt estimations, but measuring additional distances detrimentally increases the cycle time of manufacturing component 10.

Transducer 36 (FIG. 2) is a portion of a sonographic tool that converts or transforms an electrical signal into an acoustic signal or acoustic wave 50. Transducer 36 overlies corner 40 at end 44 of substrate 22. Transducer 36 directs wave 50 towards and into package 11 near corner 40 of substrate 22. A region of surface 32 reflects a portion 51 of wave 50 away from package 11 and towards an acoustic detector (not shown) in proximity to transducer 36. The remaining portion of wave 50 continues into or through package 11 towards substrate 22, and a region of corner 40 on surface 33 reflects a portion 52 of wave 50 away from substrate 22 and towards the acoustic detector. Next, transducer 36 is moved to a different position over opposite corner 41 of surface 33. Then, transducer 36 directs an acoustic signal or acoustic wave 53 towards and into package 11 near corner 41 of surface 33. A different region of surface 32 reflects a portion 54 of wave 53 toward the acoustic detector. The remaining portion of wave 53 continues into or through package 11 towards substrate 22, and a region of corner 41 on surface 33 reflects a portion 55 of wave 53 away from substrate 22 and towards the acoustic detector. For accurate measurement of distances 34 and 35, waves 50 and 53 are preferably similar to each other and are preferably approximately perpendicular to surface 32 of package 11. For similar reasons, the region of surface 32 that reflects portion 51 of wave 50 preferably directly overlies the region of corner 40 that reflects portion 52 of wave 50, and the region of surface 32 that reflects portion 54 of wave 53 preferably directly overlies the region of corner 41 that reflects portion 55 of wave 53.

Figure 3:
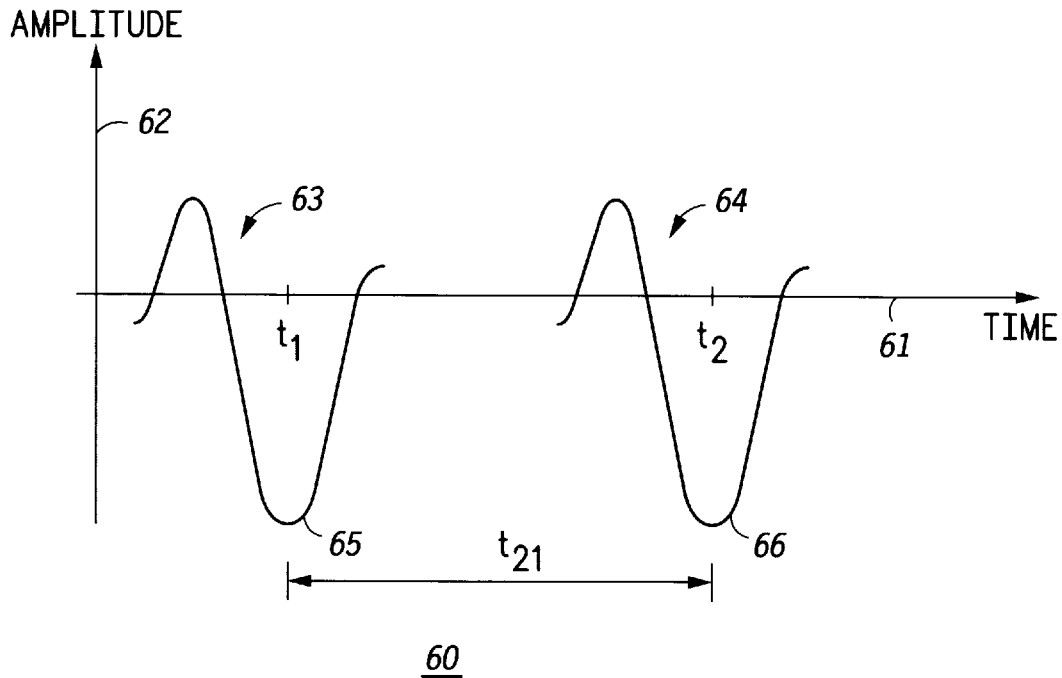
FIGS. 3 and 4 depict graphs of a time of flight representation of substrate tilt within the packaged semiconductor component of FIG. 2 in accordance with the present invention.
Figure 4:
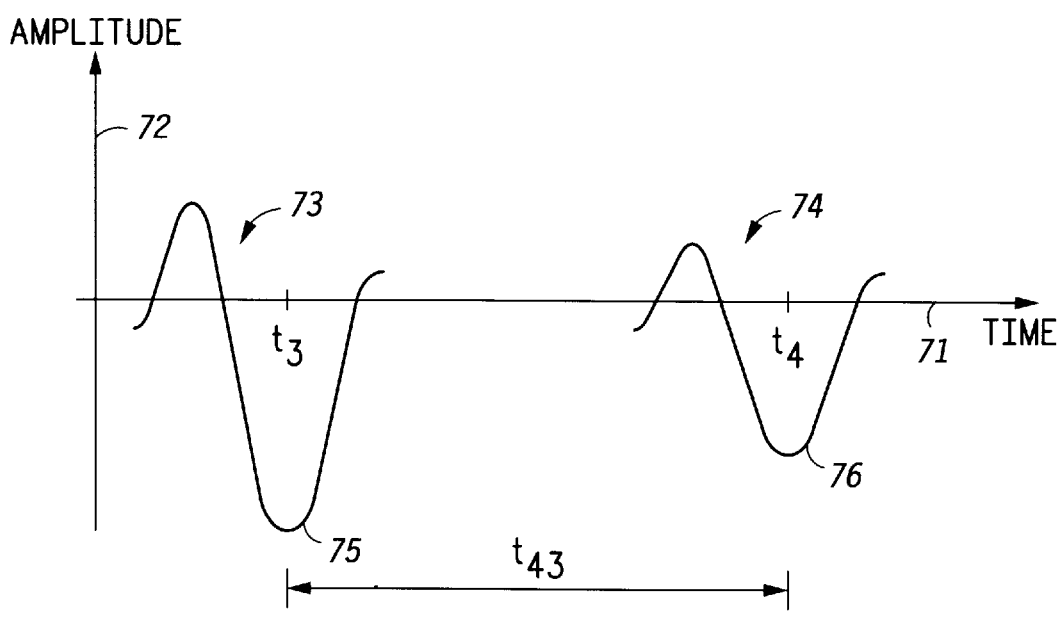

FIGS. 3 and 4 depict graphs 60 and 70, respectively, which illustrate a time of flight representation of substrate tilt within component 10 of FIG. 2. FIGS. 3 and 4 have abscissa or x-axes 61 and 71, respectively, that represent time. X-axes 61 and 71 are not drawn to scale with each other. FIGS. 3 and 4 also have ordinate or y-axes 62 and 72, respectively, that represent the amplitude of the reflected acoustic waves detected by the acoustic detector. Graphs 60 and 70 depict the reflected waves that are acoustically detected over corners 40 and 41, respectively, of substrate 22 (FIG. 2). In FIG. 3, signals 63 and 64 represent reflected portions 51 and 52, respectively, of wave 50 (FIG. 2). Similarly, in FIG. 4, signals 73 and 74 represent reflected portions 54 and 55, respectively, of wave 53 (FIG. 2). The timing of signals 63, 64, 73, and 74 are measured from peaks 65, 66, 75, and 76, respectively, and occur at times t1, t2, t3, and t4, respectively. It is understood that the exact shapes or waveforms of signals 63, 64, 73, and 74 are dependent upon the hardware or equipment used to emit and detect signals 63, 64, 73, and 74.

A difference in time between signals 63 and 64 of FIG. 3 represents the amount of time required for wave 50 to pass through surface 32 and into package 11 (FIG. 2), to reflect off of surface 33 (FIG. 2), and to exit package 11 from surface 32. Similarly, a difference in time between signals 73 and 74 of FIG. 4 represents the amount of time required for wave 53 to pass through surface 32 and into package 11, to reflect off of surface 33, and to exit package 11 from surface 32. The differences in time between signals 63 and 64 and between signals 73 and 74 are represented as distances in time t21 and t43, respectively. Accordingly, times t21 and t43 can be correlated or converted to a measurement of distances 34 and 35 (FIG. 2), respectively. This correlation or conversion can be accomplished by using equation 1 (eq. 1) wherein "Distance" represents measured distances 34 or 35, wherein "Time" represents times t21 or t43, and wherein "Velocity" represents the velocity or speed of waves 50 and 53. The velocity of waves 50 and 53 is $$\text{Distance} = \frac{\text{Time} * \text{Velocity}}{2} \qquad \text{(eq. 1)}$$

dependent upon the composition and density of package 11 and is known to those skilled in the art. When times t21 and t43 are approximately equal to each other, then distances 34 and 35 of FIG. 2 are also approximately equal to each other so that substrate tilt does not exist within component 10. However, when time t21 is greater than time t43, then distance 34 is greater than distance 35, and substrate tilt is present within component 10. Furthermore, when time t21 is less than time t43, then substrate tilt is also present within component 10, but in this case, distance 34 is less than distance 35. When waves 50 and 53 have frequencies of approximately 50 to 75 megahertz and when distances 34 and 35 are approximately 150 to 350 microns, typical values for times t21 and t43 are approximately zero to one hundred nanoseconds.

After calculating distances 34 and 35 from eq. 1, distance 34 is subtracted from distance 35, or vice versa, and the difference between distances 34 and 35 is compared to a predetermined threshold value. If the calculated difference is greater than the threshold value, then the degree of substrate tilt in component 10 is too large, and component 10 is discarded. However, if the calculated difference is less than the threshold value, then the degree of substrate tilt is within an acceptable limit, and component 10 can be electrically tested or delivered to a customer.

As discussed previously, when the substrate tilt needs to be characterized in three dimensions, then a third distance should be measured in component 10. As an example, the third distance can be measured near either of corners 42 or 43 (FIG. 1) of substrate 22. Combined with distances 34 and 35, the third distance can be used to determine a plane of substrate 22 using techniques known in the art. Then, the calculated plane of substrate 22 can be compared to a predetermined reference plane to determine if the degree of substrate tilt exceeds an allowable or permissible limit. As stated earlier, if the calculated value or plane is greater than the reference value or plane, then component 10 is discarded. However, if the calculated plane is less than the reference plane, then component 10 can be electrically tested or shipped to a customer.

Figure 5:
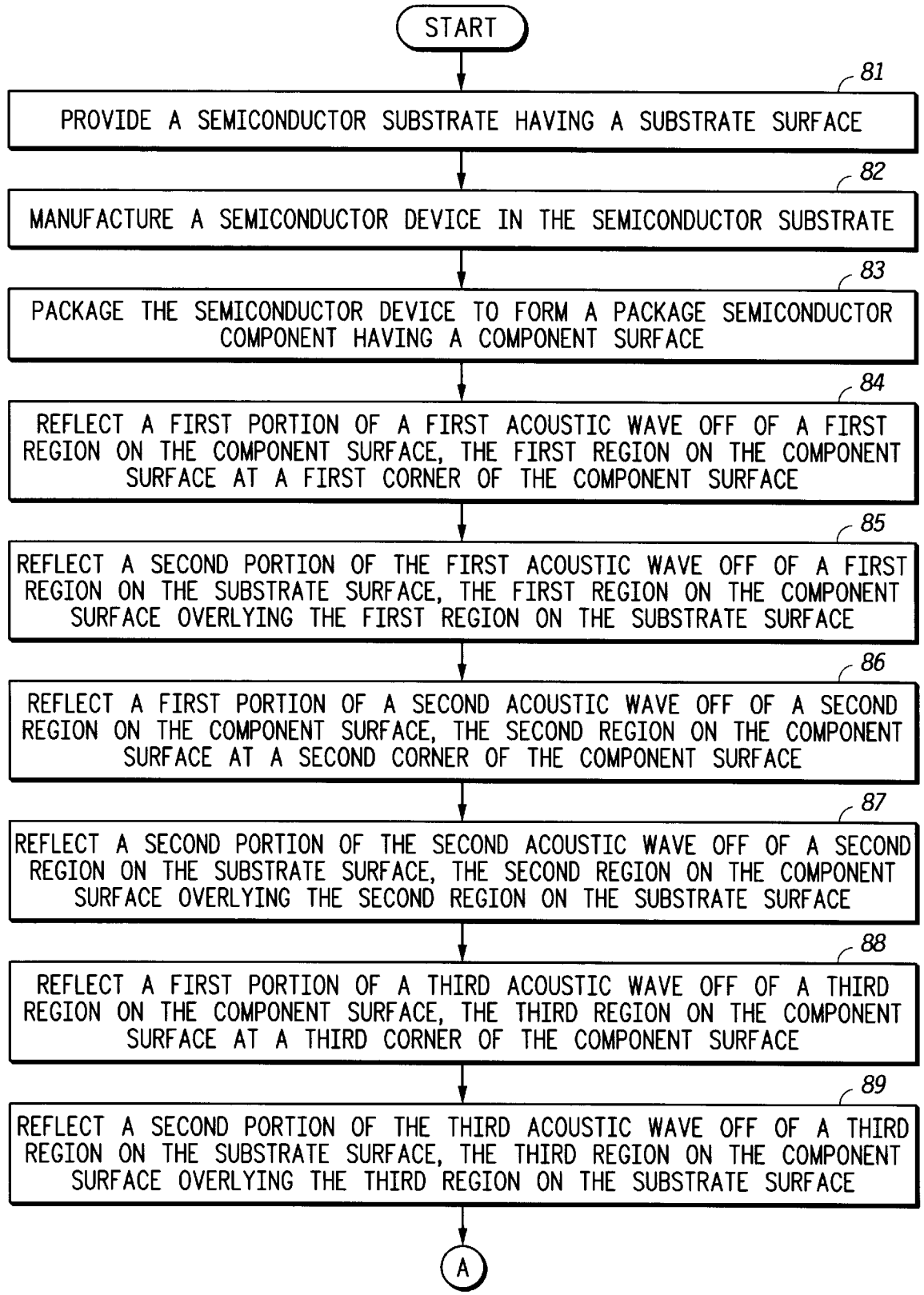
FIG. 5 and FIG. 6 are a flow chart outlining a method of manufacturing the packaged semiconductor component in accordance with the present invention.
Figure 6:
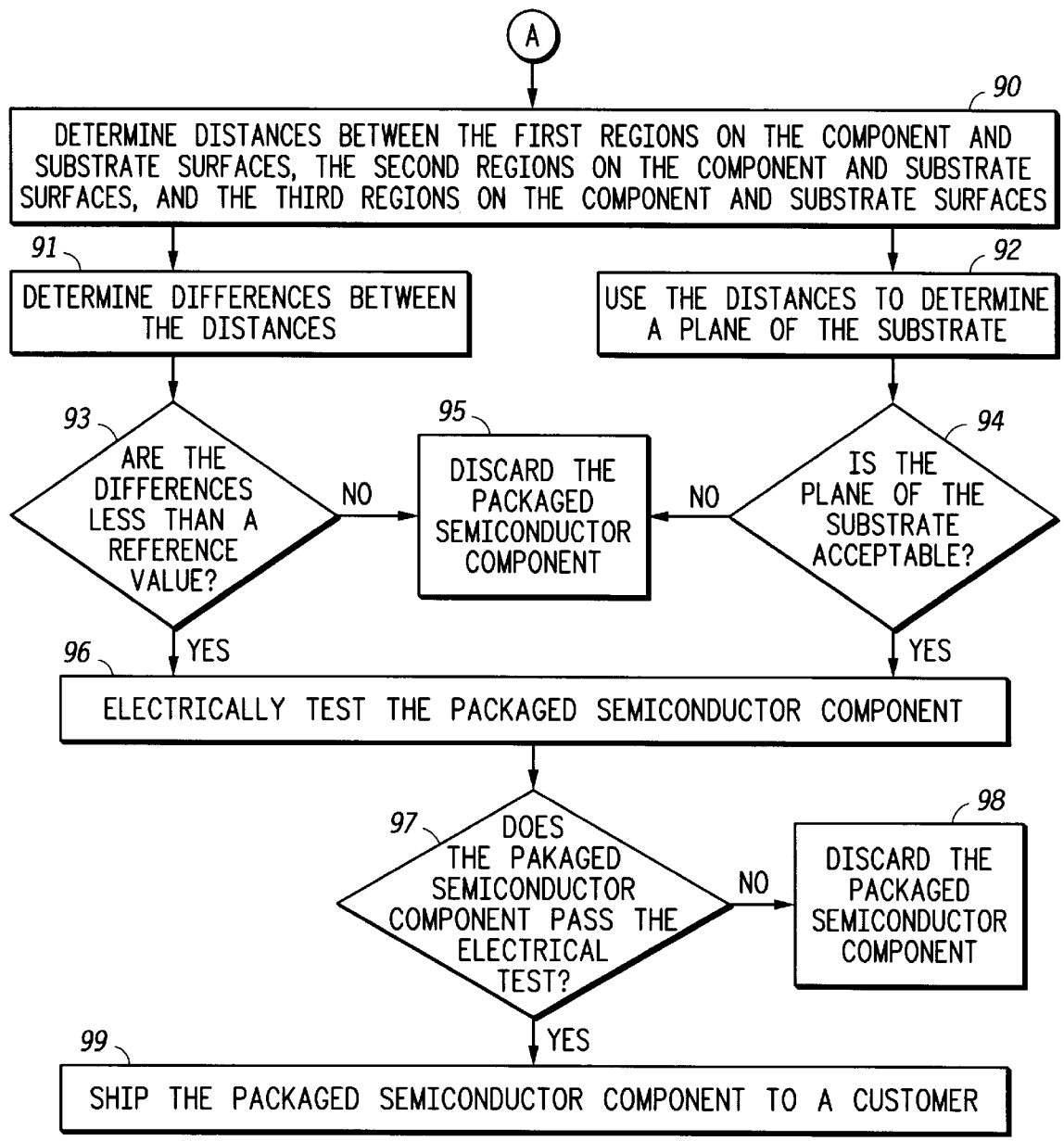

FIG. 5 is a flow chart 80 outlining a method of manufacturing or fabricating component 10, as described hereinbefore with reference to FIGS. 1, 2, 3, and 4. A substrate such as, for example, substrate 22 (FIG. 2) is provided in a step 81 of flow chart 80. Then, a device or circuit such as, for example, circuit 31 (FIG. 2) is manufactured in the substrate during a step 82. Next, the circuit is packaged to form a packaged component such as, for example, component 10 (FIG. 2) during a step 83. Step 83 includes coupling the substrate to a leadframe such as, for example, leadframe 12 (FIG. 2). Subsequently, in steps 84, 85, 86, 87, 88, and 89, three acoustic waves are reflected off of a surface of the packaged component and are also reflected off of a surface of the substrate. Then, during a step 90 (found in FIG. 6), distances between the surface of the packaged component and the surface of the substrate are determined from the reflections of the acoustic waves in steps 84 through 89.

If a two dimensional determination of substrate tilt is required, then steps 91 and 93 can be performed to determine differences between the calculated distances and to compare the differences to a threshold or reference value. When steps 91 and 93 are performed, then steps 89 and 90 are optional. However, if a three dimensional determination of substrate tilt is preferred, then steps 92 and 94 can be performed in place of steps 91 and 93 to use the calculated distances to determine a plane of the substrate and to compare the calculated plane of the substrate to a reference plane or value.

If the calculated values of steps 91 or 92 exceed the reference values of steps 93 or 94, respectively, then the packaged component of step 83 is discarded during a step 95. However, if the reference values of steps 93 or 94 exceed the calculated values of steps 91 or 92, then the packaged component is kept and can be electrically tested during a step 96. Then, a decision is made in a step 97 to discard the packaged component during a step 98 if the packaged component fails the electrical tests of step 96. However, if the packaged component passes the electrical tests, then the packaged component can be shipped to a customer during a step 99. It is understood that the electrical tests of step 96 can be performed before or after the substrate tilt measurement of steps 84 through 94.

Therefore, it is apparent there has been provided an improved method of determining substrate tilt within a packaged component that overcomes the disadvantages of the prior art. The present method is non-destructive because the packaged component does not need to be physically cut open, as in the prior art. Furthermore, the method described herein is compatible with a manufacturing process because of the non-destructive nature of the method and because the method does not significantly increase the cycle time required for fabricating a semiconductor component.

While the invention has been particularly shown and described with reference to preferred embodiments, it will be understood by those skilled in the art that changes in form and detail may be made without departing from the spirit and scope of the invention. For instance, the numerous details set forth herein such as, for example, the specific locations on surface 33 (FIG. 2) used to determine substrate tilt are provided to facilitate the understanding of the present invention and are not provided to limit the scope of the invention. As an example, substrate tilt can be determined by measuring distances between surfaces 32 and 33 (FIG. 2) at positions other than corners 40 and 41 (FIG. 2). These other positions include, but are not limited to, the middle regions of ends 44 and 45 (FIG. 1) between corners 40 and 42 and between corners 41 and 43. Furthermore, substrate tilt can be determined by measuring distances between substrate 13 and the bottom exterior surface of package 11. Moreover, substrate tilt can be evaluated by measuring a distance between substrate 22 and a reference surface different from top surface 32 or the bottom surface of package 11. Yet another alternative embodiment uses the method of determining substrate tilt as a process monitor in a manufacturing environment for a high pressure transfer molding process. When significant amounts of substrate tilt are detected, the molding process is adjusted or modified to reduce or eliminate the substrate tilt of subsequently packaged components. In addition to detecting substrate tilt, the method described herein can also be used to determine the position or height of substrates 13 or 22 within package 11. Accordingly, the disclosure of the present invention is not intended to be limiting. Instead, the disclosure of the present invention is intended to be illustrative of the scope of the invention, which is set forth in the following claims.

We claim:

1. A non-destructive method of determining substrate tilt within a packaged semiconductor component comprising:

providing the packaged semiconductor component having a surface;

providing a substrate in the packaged semiconductor component, the substrate having first and second ends opposite each other, the substrate having a surface coupling the first and second ends;

using a first acoustic wave to measure a first distance from the surface of the packaged semiconductor component to the surface of the substrate at the first end of the substrate;

using a second acoustic wave to measure a second distance from the surface of the packaged semiconductor component to the surface of the substrate at the second end of the substrate; and comparing the first and second distances to a threshold value.

2. The method of claim 1 wherein the steps of using the first acoustic wave and using the second acoustic wave include using scanning acoustic microscopy.

3. The method of claim 1 wherein the step of using the first acoustic wave includes measuring a distance between a first reflection in the first acoustic wave and a second reflection in the first acoustic wave.

4. The method of claim 1 wherein the step of using the first acoustic wave includes measuring a difference in time between a first acoustic reflection and a second acoustic reflection and wherein the step of using the second acoustic wave includes measuring a difference in time between a third acoustic reflection and a fourth acoustic reflection.

5. The method of claim 4 wherein the step of using the first acoustic wave includes converting the difference in time between the first acoustic reflection and the second acoustic reflection to a measurement of the first distance and wherein the step of using the second acoustic wave includes converting the difference in time between the third acoustic reflection and the fourth acoustic reflection to a measurement of the second distance.

6. The method of claim 5 wherein the step of comparing the first and second distances includes comparing the threshold value to a difference between the measurements of the first and second distances.

7. The method of claim 1 wherein the step of providing the substrate includes providing the substrate with at least three corners and further comprising using positions of the at least three corners to determine a plane of the substrate wherein the step of comparing the first and second distances includes comparing the plane of the substrate to a reference plane.

8. The method of claim 1 wherein the step of using the first acoustic wave includes providing the first distance approximately perpendicular to the surface of the packaged semiconductor component and wherein the step of using the second acoustic wave includes providing the second distance approximately perpendicular to the surface of the packaged semiconductor component.

9. The method of claim 1 wherein the step of using the first acoustic wave includes using a time of flight method to measure the first distance and wherein the step of using the second acoustic wave includes using a time of flight method to measure the second distance.

10. A method of fabricating a component comprising:

providing a substrate;

providing a package around the substrate wherein an interface exists between the substrate and the package and wherein the package has a surface and wherein the interface has a plurality of corners; and acoustically detecting a position of the interface by measuring at least two distances between the interface and the surface wherein the at least two distances are measured near different ones of the plurality of corners.

11. The method of claim 10 wherein the step of acoustically detecting the position of the interface includes measuring a time of flight of an acoustic wave.

12. The method of claim 10 wherein the step of acoustically detecting the position of the interface includes measuring less than three distances between the interface and the surface wherein the less than three distances are measured near different ones of the plurality of corners and wherein the less than three distances are comprised of the at least two distances.

13. The method of claim 10 further comprising electrically operating the component after the step of acoustically detecting the position of the interface.

14. A method of manufacturing a semiconductor component comprising:

providing a semiconductor substrate having a substrate surface;

manufacturing a semiconductor device in the semiconductor substrate;

packaging the semiconductor device to form a packaged component, the packaged component having a component surface, the component surface having a first end and a second end opposite the first end;

reflecting a first portion of a first acoustic wave off of a first region on the component surface, the first region on the component surface being at the first end of the component surface;

reflecting a second portion of the first acoustic wave off of a first region on the substrate surface, the first region on the component surface overlying the first region on the substrate surface;

determining a first distance between the first region on the component surface and the first region on the substrate surface;

reflecting a first portion of a second acoustic wave off of a second region on the component surface, the second region on the component surface being at the second end of the component surface;

reflecting a second portion of the second acoustic wave off of a second region on the substrate surface, the second region on the component surface overlying the second region on the substrate surface;

determining a second distance between the second region on the component surface and the second region on the substrate surface;

determining a difference between the first distance and the second distance; and comparing a predetermined threshold value and the difference between the first distance and the second distance.

15. The method of claim 14 wherein the steps of reflecting the first portion of the first acoustic wave, reflecting the second portion of the first acoustic wave, reflecting the first portion of the second acoustic wave, and reflecting the second portion of the second acoustic wave include using scanning acoustic tomography.

16. The method of claim 14 wherein the step of packaging the semiconductor device includes using a transfer molding process to form the packaged component.

17. The method of claim 14 wherein the step of packaging the semiconductor device includes providing a first corner at the first end of the component surface and providing a second corner at the first end of the component surface wherein the step of determining the first distance comprises:

determining a distance between the first region on the component surface and the first region on the substrate surface, the first region on the component surface being near the first corner of the component surface; and determining a distance between a third region on the component surface and a third region on the substrate surface, the third region on the component surface being near the second corner of the component surface, and the third region on the component surface overlying the third region on the substrate surface.

18. The method of claim 17 wherein the step of determining the difference between the first distance and the second distance includes using the second distance, the distance between the first region on the component surface and the first region on the substrate surface, and the distance between the third region on the component surface and the third region on the substrate surface to determine a plane of the substrate surface and wherein the step of comparing the predetermined threshold value includes comparing the plane of the substrate surface to a predetermined reference plane.

19. The method of claim 14 further comprising adjusting a molding process when the difference between the first distance and the second distance exceeds the predetermined threshold value.

20. A method of manufacturing a semiconductor component comprising:

providing a semiconductor substrate having a substrate surface;

manufacturing a semiconductor device in the semiconductor substrate;

packaging the semiconductor device to form a packaged component, the packaged component having a component surface, the component surface having a first end and a second end opposite the first end, the first end having first and second corners;

reflecting a first portion of a first acoustic wave off of a first region on the component surface, the first region on the component surface being at the first end of the component surface;

reflecting a second portion of the first acoustic wave off of a first region on the substrate surface, the first region on the component surface overlying the first region on the substrate surface;

determining a first distance between the first region on the component surface and the first region on the substrate surface, wherein determining the first distance comprises (i) determining a distance between the first region on the component surface and the first region on the substrate surface, the first region on the component surface being near the first corner of the component surface, and (ii) determining a distance between a third region on the component surface and a third region on the substrate surface, the third region on the component surface being near the second corner of the component surface, and the third region on the component surface overlying the third region on the substrate surface;

reflecting a first portion of a second acoustic wave off of a second region on the component surface, the second region on the component surface being at the second end of the component surface;

reflecting a second portion of the second acoustic wave off of a second region on the substrate surface, the second region on the component surface overlying the second region on the substrate surface;

determining a second distance between the second region on the component surface and the second region on the substrate surface;

determining a difference between the first distance and the second distance, wherein the step of determining the difference between the first distance and the second distance comprises (i) determining a difference between the second distance and the distance between the first region on the component surface and the first region on the substrate surface, (ii) determining a difference between the second distance and the distance between the third region on the component surface and the third region on the substrate surface, and (iii) determining a difference between the distance between the first region on the component surface and the first region on the substrate surface and the distance between the third region on the component surface and the third region on the substrate surface; and comparing a predetermined threshold value and the difference between the first distance and the second distance, wherein the step of comparing the predetermined threshold value includes comparing the predetermined threshold value to the difference between the second distance and the distance between the first region on the component surface and the first region on the substrate surface, the difference between the second distance and the distance between the third region on the component surface and the third region on the substrate surface, and the difference between the distance between the first region on the component surface and the first region on the substrate surface and the distance between the third region on the component surface and the third region on the substrate surface.

\* \* \* \* \*